United States Patent [19]
Murray

[11] Patent Number: 5,710,047
[45] Date of Patent: Jan. 20, 1998

[54] METHOD FOR MONITORING GROWTH AND DETECTION OF ENVIRONMENTAL STRESS IN PLANTS

[75] Inventor: Allen K. Murray, Newport Beach, Calif.

[73] Assignee: Glycozyme, Inc., Irvine, Calif.

[21] Appl. No.: 516,953

[22] Filed: Aug. 18, 1995

[51] Int. Cl.$^6$ .................................................. G01N 33/68
[52] U.S. Cl. .............................. 436/94; 436/174; 47/58
[58] Field of Search ........................... 47/58.01, 58.17, 47/58, 1; 436/94, 161, 174

[56] References Cited

U.S. PATENT DOCUMENTS

| | | |
|---|---|---|
| 4,094,845 | 6/1978 | De Long. |
| 4,755,942 | 7/1988 | Gardner et al. |
| 4,876,647 | 10/1989 | Gardner et al. |
| 4,998,826 | 3/1991 | Wood et al. |
| 5,042,294 | 8/1991 | Uzzell. |

OTHER PUBLICATIONS

Biosis 87:81257, 1986.

Timpa et al., "Monitoring Organic Acids and Carbohydrates in Cotton Leaves by High Performance Liquid Chromatography," J. Agric. Food. Chem., 1986, 34, 910–913.

Timpa et al., "Effects of Water Stress on the Organic Acid and Carbohydrate Compositions of Cotton Plants", Plant Physiol. (1986)82, 724–728.

E.-D. Schulze, "Carbon Dioxide and Water Vapor Exchange in Response to Drought in the Atmosphere and in the Soil", Ann. Rev. Plant Physiol, 1986 37:247–74, 1986 by Annual Reviews, Inc.

J.M. Virgona, et al., "Drought Stress Induces Changes in the Non-structural Carbohydrate Composition of Wheat Stems", Aust. J. Plant Physiol, 1991, 18, 239–247.

James E. Morgan, "Osmoregulation and Water Stress in Highher Plants", Ann. Rev. Plant Physiol, 1984, 35:299–319, 1984 by Annual Reviews, Inc.

Janusz J. Zwiazek, "Cell Wall Changes in White Spruce (*Picea glauca*) Needles Subjected to Repeated Drought Stress", 36 Physiologia Plantarum 82: 513–518, Copenhagen 1991.

James R. Frederick, et al., "Carbohydrate, Nitrogen and Dry Matter Accumulation and Partitioning of Maize Hybrids Under Drought Stress", Annals of Botany 66, 407–415, 1990.

J.P. Thornber, et al., "Changes in the Chemical Composition of a Cambial Cell during its Differentiation into Xylem and Pholem Tissue in Trees", Biochem. J. (1962) 82, 340.

Deborah P. Delmer, et al., "Utilization of Nucleoside Diphosphate Glucoses in Developing Cotton Fibers", Plant Physiol. (1974) 53, 149–153.

Christopher T. Brett, "Polysaccharide Synthesisfrom GDP Glucose in Pea Epicotyl Slices", Journal of Experimental Botany, vol. 32, No. 130 pp. 1067–1077, Oct. 1981.

G. Piro, et al., "Glucomannan synthesis in Pea epicotyls: The mannose and glucose transterases", Planta (1993) 190:206–220.

A.D. Elbein, "Biosynthesis of a Cell Wall Glucomannan in Mung Bean Seedlings", The Journal of Biological Chemistry, vol. 224, No. 6, Issue of Mar. 25, pp.1608–1916, 1969.

(List continued on next page.)

Primary Examiner—Lyle A. Alexander
Attorney, Agent, or Firm—Graham & James, LLP

[57] ABSTRACT

A method of detecting environmental stress in plants, particularly water stress in cotton plants is based on a cold water extraction of plant tissues such as cotton fibers. The extract is analyzed by high pH anion exchange chromatography to separate and characterize the saccharides, oligosaccharides and other glycoconjugates extracted by cold water. The extracted carbohydrates represent a uniquely sensitive means to detect environmental stress. Environmentally stressed plants show both a qualitative and quantitative alteration of the extracted carbohydrates. The alteration in extracted carbohydrates can be used to indicate when additional irrigation or other correction to the growth conditions is required.

13 Claims, 12 Drawing Sheets

OTHER PUBLICATIONS

C.L. Villemez, et al., "Is Guanosine Diphosphate–D–Glucose a Precursor of Cellulose", Nature vol. 227, Jul. 4, 1970, pp. 80–81.

C.L. Villemez, "Rate Studies of Polysaccharide Biosynthesis from Guanosine Diphosphate a–D–Glucose and Guanosine Diphosphate a–D–Mannose", Biochem. J. (1971) 121, pp. 151–157.

C.L. Villemez, "Characterization of Intermediates in Plant Cell Wall Biosynthesis", Biochemical and Biophysical Research Communications, vol. 40, No. 3, 1970, pp. 636–641.

J.S. Heller, et al., "Solubilization of a Mannose–Polymerizing Enzyme from *Phaselus aureus*", Biochem. J. (1972) 128 pp. 243–252.

J.S. Heller et al., "Interaction of Soluble Glucosyl–and Mannosyl– Transferase Enzyme Activities in the Synthesis of a Glucomannan", Biochem. J. (1972) 129, pp. 645–655.

C.L. Villemez, "Molecular Sieve Chromatography of Biosynthetic Cell ($^{14}C$) Glucomannan Chains", Archives of Biochemistry and Biophysics, 165, pp. 407–412 (1974).

Alejandra A. Covarrubias, et al., "Cell–Wall Proteins Induced by Water Deficit in Bean (*Phaseolus vulgaris* L.) Seedlings", Plant Physiol (1995) 107: pp. 1119–1128.

David M. Gilbeaut, et al., "Biosynthesis of Plant Cell Wall Polysaccharides", The FASEB Journal, vol. 8, Sep. 1994, pp. 904–915.

Dave Guthrie, "Peak Bloom", Cotton Physiology Today, vol. 6, No. 5, Jul., 1995 pp. 1–4.

Dionex, "Analysis of Carbohydrates by High Performance Anion Exchange Chromatography with Pulsed Amperometric Detection (HPAE–PAD)", Technical Note 20, 12/92, 1993 Dionex Corporation.

Dionex, "Optimal Settings for Pulsed Amperometric Detection of Carbohydrates Using Dionex Pulsed Electrochemical and Amperometric Detectors", Technical Note 21, 10/94, 1994 Dionex Corporation.

Daniel R. Krieg, et al., "Source–Sink Relations as Affected by Water Stress During Boll Development", Cotton Physiology, No. 1 (1986) Chpt. 8, pp. 73–77.

Harry R. Lefflet, "MIneral Compartmentation within the Boll", Cotton Physiology, No. 1 (1986) Chpt. 21, pp. 301–309.

A. Michael Schubert, et al., "Carbohydrate Distribution in Bolls", Cotton Physiology, No. 1 (1986) Chpt. 22, pp. 311–324.

Edmond A.L. DeLanghe, "Lint Development", Cotton Physiology, No. 1 (1986) Chapt. 23, pp. 325–349.

Harmon H.Ramey, Jr., "Stress Influences on Fiber Development", Cotton Physiology, No. 1 (1986) Chpt. 24, pp. 351–359.

Daniel S. Munk, et al., "Plant Responses to Water Deficits in Cotton", currently is press, Proceedings: World Cotton Research Conference I, Brisbane, Australia, Feb. 14–17, 1994.

METHOD FOR MONITORING GROWTH AND DETECTION OF ENVIRONMENTAL STRESS IN PLANTS

BACKGROUND OF THE INVENTION

1. Field of the Invention

This invention concerns a method of detecting environmental stress in green land plants, particularly in agricultural crops, so that production can be optimized by alleviating the stress before permanent damage to the plants occurs.

2. Description of Related Art

The vast majority of living organisms are directly or indirectly dependent on photosynthesis. That is, photosynthetic organisms capture the energy of sunlight through the process of photosynthesis storing the energy in the form of organic molecules which serve as a food source for those living organisms which are not capable of photosynthesis.

Human civilization is strongly dependent upon agricultural green lands plants for food and fiber, as well as a source of many important organic chemicals. Other photosynthetic organisms, such as trees, provide building materials and the like.

Green land plants are marvelous food factories needing only light, water, and a few soil minerals to fix atmospheric carbon dioxide into organic molecules. Although most of us remain ignorant of the factors necessary for optimal plants growth, farmers are aware of a myriad of things that can reduce or destroy a growing crop. Insect pests chew on plant tissues or suck plant juices. Various pathogens stunt or kill plants, while deficiencies of key soil minerals slow or prevent plant growth. Other less desirable plants (weeds) out compete crop plants. There may be insufficient (or excessive) soil moisture and the air temperature may be too hot or too cold for optimal growth.

While all of the above factors may and do exert stress upon a growing plant, some stress factors such as the presence of insect pests are relatively easy to detect (usually visually) and remedy (usually with pesticides). Some plant pathogens are more difficult to detect and are best prevented by growing only genetically resistant strains of crop plants. Mineral nutrition of green land plants is generally well understood and a relatively simple soil test allows one to determine which soil minerals should be supplemented (in the form of fertilizer) and how much of the supplement should be used. Optimal growing temperatures are also well studied, but except for the case of greenhouse-grown plants, growth temperature is usually beyond human control.

This leaves water as the single most critical controllable factor in optimal plant growth. Like many good things, water can be easily overdone, leading to damage to plant roots as the excess water excludes oxygen from the soil. However, the usual problem is one of insufficient water. Green land plants use water as a "circulatory" medium to transport soil minerals from the roots to the photosynthetic leaves where such minerals are required for various aspects of photosynthesis and cell growth, as well as to transport photosynthates (sugars) from the leaves to all nonphotosynthetic tissues of the plant.

Furthermore, the entire plant body of herbaceous plants and the leaves of woody plants are hydraulically supported so that the plant collapses (wilts) if there is a water shortage. Such wilting greatly impacts photosynthesis, since crumpled leaves do not perform as efficient light-absorbing surfaces. Further, the atmospheric carbon dioxide that is fixed into organic molecules through photosynthesis enters the leaf through pores known as stomata. When a plant is deficient in water, the stomata automatically close to slow water loss through evaporation (transpiration). This, in turn, limits the entry of carbon dioxide needed for photosynthesis. See, for example "Carbon Dioxide and Water Vapor Exchange in Response to Drought in the Atmosphere and in the Soil," *Ann. Rev. Plant Physiol.* 37:247–74 (1986); and "Carbohydrate, Nitrogen and Dry Matter Accumulation and Partitioning of Maize Hybrids Under Drought Stress," *Annals of Botany* 66:407–15 (1990).

The real problem, then, is how to decide when enough water is provided to avoid stress and maximize plant growth without wasting often scarce water resources. In addition, many localities have water supplies containing salts such as sodium chloride which accumulate in the soil, ultimately causing plant damage. Obviously, one does not wish to apply more than the optimal amount of water, since excess applications will only increase the rate of accumulation of salts in the soil.

It is relatively simple to weigh a sample of soil and calculate how much water is present. But different types of soil bind water with different affinities and plant roots penetrate to different depths, depending both on soil structure and plant types. Thus, a measurement of water in a sample of surface soil is of relatively little use in predicting the presence or absence of drought-induced stress in growing plants. It is also possible to measure a factor called water potential within a plant. Water potential gives a measure of the tendency of water to move into the plant from the soil, but this factor is also difficult to relate to plant stress.

Finally, there have been a number of attempts to quantitate plant water stress by measuring plant leaf temperature and/or by making comparisons between air temperature and leaf temperature. Basically, a plant leaf exposed to sunlight absorbs a great deal of solar energy, only a fraction of which is captured through photosynthesis; the remaining energy appears as heat, tending to increase the temperature of the leaf. At the same time, leaves lose a large amount of water through their stomata; the resulting evaporative cooling tends to moderate temperature increases caused by light absorption. Thus, all other things being equal, a higher leaf temperature reflects a lower availability of water (i.e., drought stress). Of course, many other factors such as relative humidity of the surrounding air must be taken into account.

For an example demonstrating the use of leaf temperature to predict drought stress, see U.S. Pat. No. 4,998,826 to Wood et al., which describes an infrared thermometer designed for agricultural use. This patent teaches that there is a narrow window of leaf temperature that results in optimal plant growth. The patent also teaches that water should be applied to the field whenever the leaf temperature rises above the optimal temperature window. However, it is known that leaf temperature is also affected by relative humidity of the surrounding air, as well as numerous other factors. In addition, it is often difficult in advance to predict what will be the optimal leaf temperature. That is, even if the temperature measurement is corrected for all other factors, it is difficult to know whether a given temperature was optimal until after crop damage has occurred.

U.S. Pat. Nos. 4,755,942 and 4,876,647 to Gardner et al. attempt to improve the predictive accuracy of determining water stress in crop plants by simultaneously measuring a number of different factors including crop canopy (leaf) and air temperatures and relative humidity. A microcomputer running a specialized program analyzes the various factors and makes stress predictions based on prerecorded data concerning the stress factors of the particular crop at hand. Again, a major problem is that it is extremely difficult to predict which values of combined factors actually represent drought stress for a particular species or variety of plants. Without knowing what values actually represent stress, complex multifactorial measurements are virtually useless.

SUMMARY OF THE INVENTION

It is an object of the present invention to provide a method for detecting environmental stress in plants by analyzing the glycoconjugate and oligosaccharide precursors of plant cell walls.

These and other objects are met by a method of detecting environmental stress in plants, particularly water stress in cotton plants. The method is based on a gentle cold water extraction of plant tissues such as cotton fibers. The extract is analyzed by high pH anion exchange chromatography to separate and characterize the saccharides, oligosaccharides and other glycoconjugates extracted by cold water. The extracted carbohydrates represent a uniquely sensitive means to detect environmental stress. Environmentally stressed plants show both a qualitative and quantitative alteration of the extracted carbohydrates. The alteration in extracted carbohydrates can be used to indicate when additional irrigation or other correction to the growth conditions is required.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
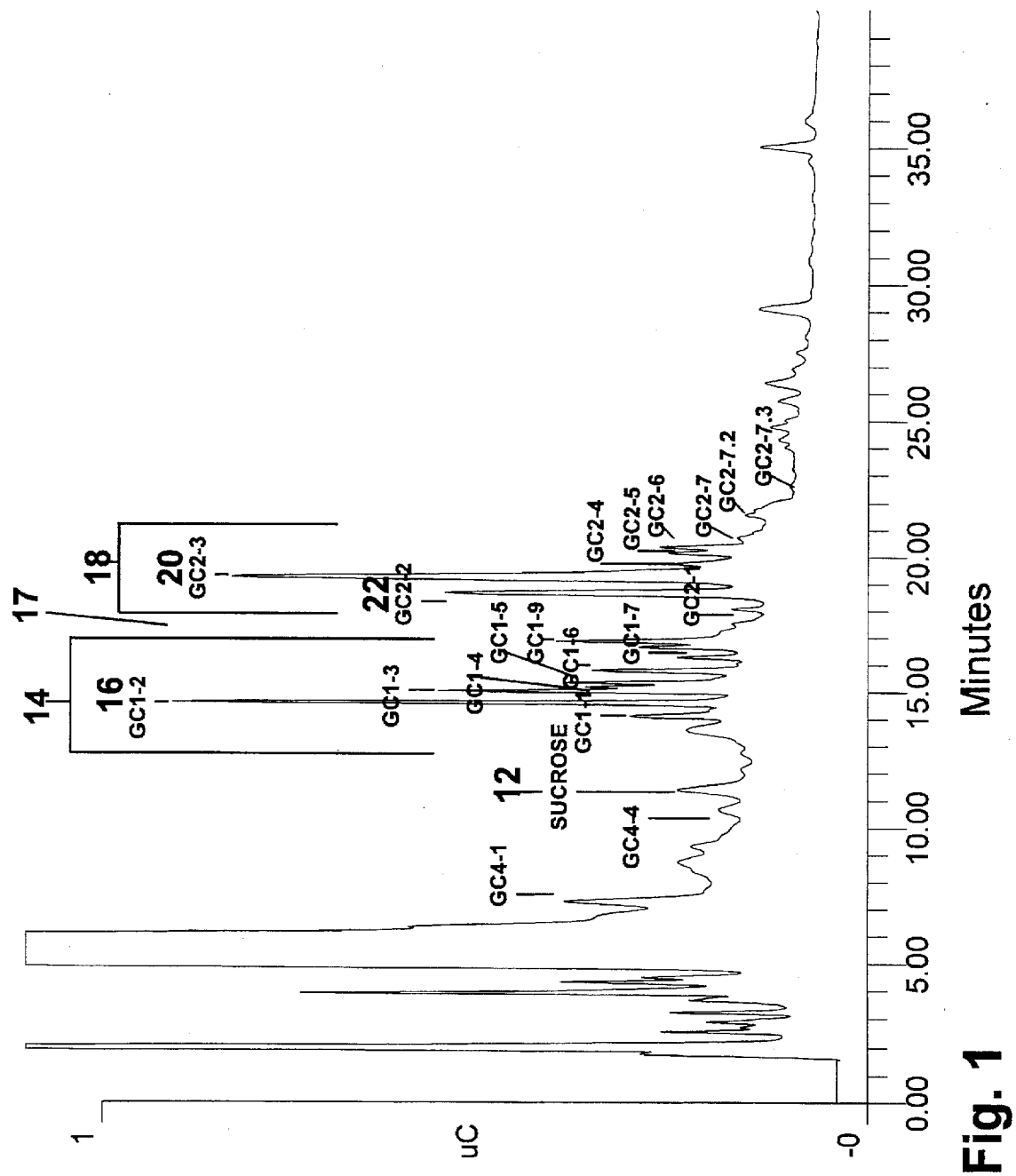
FIG. 1 shows an idealized HPAEC profile of a sample of a cold water extract of cotton fibers taken from a 21-day postanthesis boll of cotton variety DPL5415.

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a reproducible method that allows samples of plant tissue to be analyzed to determine whether the sampled plant is undergoing stress.

Applicant approached the problem of environmental stress in green land plants by considering environmental effects on the carbohydrate content of portions of the plant body. As explained above, stress tends to have a direct effect on photosynthesis and, hence, should cause an alteration in various plant carbohydrates which are directly produced by photosynthesis. Furthermore, since the body of a green land plant is primarily composed of a skeleton of carbohydrates and other organic products of photosynthesis (i.e. wood is largely cellulose combined with an organic polyphenol known as lignin), analysis of the plant body should provide a good record of carbohydrate alterations induced by stress, such as drought, on the plant.

The precise structure and composition of the cellulosic cell walls that surround plant cells and form the foundation of the plant body have not yet been completely determined. Although many chemical features of the cell walls have been delineated, the exact manner in which the cell wall is synthesized still remains somewhat of a mystery. If one is looking for alterations in plant cell walls, one must first determine what a normal cell wall looks like. A review of "Biosynthesis of plant cell polysaccharides" by Gibeaut and Carpita (*FASEB Journal*, 8:904–15 (1994)) gives a good picture of the current understanding of cell wall synthesis.

Research on plant cell walls is just beginning to confirm the idea that environmental stress, such as water stress, might affect the structure and/or composition of the plant cell wall. See "Drought stress Induces Changes in the Non-structural Carbohydrate Composition of Wheat Stems," *Aust. J. Plant. Physiol.* 18:239–47 (1991); "Cell wall changes in white spruce (*Picea glauca*) needles subjected to repeated drought stress, *Physiologia Plantarum* 82:513–18 (1991); and "Cell-Wall Proteins Induced by Water Deficit in Bean (*Phaseolus vulgaris* L.) Seedlings," *Plant Physiol.,* 107:1119–28 (1995).

Cotton is probably the world's most important fiber crop for the production of textiles. The cotton fiber is actually an extremely long (up to 4 cm) single-celled plant trichome or hair that grows attached to the developing seed of the cotton plant within a seed pod (cotton boll). The fibers come in two types: fuzz, which is a relatively short hair firmly attached to the cotton seed; and lint, which is a long fiber that can be readily separated from the cotton seed.

The fibers do not begin to develop until after the cotton flower opens (anthesis). Apparently fiber growth responds to hormones produced by embryos in the developing seeds. The fibers elongate for at least three or four weeks following opening of the flower, mostly producing what is called primary cell wall. For several weeks following fiber elongation additional cellulosic wall material is laid down, forming the secondary cell wall which strengthens the almost mature fibers. Following deposition of the secondary cell wall, the fiber cell dies at about eight weeks (56 days) postanthesis, leaving its cellulosic exoskeleton as the familiar cotton fiber of commerce.

Cotton is an extremely valuable crop plant since it produces cotton seed, a source of oil and animal feed as well as cotton fiber. The present invention was originally made while attempting to identify those components of the cell walls of cotton fibers that affected the overall fiber quality. It is known that variations in growth conditions may sharply influence the yield and the quality of a cotton crop. In fact, certain high quality cottons are somewhat limited to production in California, the Southwest, and similar climactic areas of the world. Presumably the light level or other growth factors are particularly favorable in those areas. This means that the best cotton is often grown in areas where water shortages are common.

In summer dry climates like California cotton is commonly irrigated about three times during the growing season. The irrigation consists of flooding the fields so that a considerable amount of water is consumed in the process. There is considerable evidence that too much or too little water negatively affects the production of cotton. It would be extremely valuable to know when the plants were beginning to show signs of water stress so that the next irrigation could be given at the optimum time.

While the majority of the cotton fiber cell wall consists of the polysaccharide cellulose arranged, as in most plant cell walls, in paracrystalline microfibrils, there is also a small amount of other polysaccharides that constitute either linking materials to orient and to hold the cellulose microfibrils in place and/or precursors of the microfibrils and the linking materials.

Although we now know that many of the various polysaccharides of the wall are chemically interconnected, cell wall materials have traditionally been characterized by the conditions required to extract them from the cell wall. Generally, the extraction process results in hydrolysis of at least some of the covalent bonds in the cell wall materials. Thus, the various derived fractions to some extent represent relatively simple breakdown products of a complex wall structure. Chelating agents or hot dilute acids extract various galacturonic acid containing polymers known as pectic materials. Additional noncellulosic polysaccharides known as hemicelluloses can be extracted by strong alkali while the true cellulose resists solution even in strong alkali.

Presently, greatly improved techniques of High Pressure Liquid Chromatography (HPLC) allow resolution of various cell wall fractions into constituent polysaccharides which can be further hydrolyzed to identify the constituent monosaccharides. The use of high pH artion exchange chromatography (HPAEC) makes possible the unambiguous identification of cell wall constituents. In HPAEC a salt gradient (such as a sodium acetate gradient) is applied to a column of special ion exchange resins held at a high pH to sequentially elute various mono and polysaccharides. Essentially, the hydroxyl groups of the sugars act as extremely weak acids which become deprotonated at the high pH, binding to the ion exchange matrix until eluted by the gradient.

While there are a number of vendors of HPAEC materials, the current invention has employed products and systems produced by the Dionex Corporation of Sunnyvale, Calif. These products and systems are explained in full in the Dionex Technical Notes, particularly in Technical Notes 20 and 21, which are hereby incorporated into this application.

The carbohydrate fractions isolated from plant cell walls were analyzed using Dionex CarboPac PA1 and PA-100 columns. Both of these columns contain polystyrene/divinylbenzene cross-linked latex microbeads (350 nm diameter) with quaternary amine functional groups. The columns were operated under the manufacturer's recommended pressure conditions (4000 psi maximum) in sodium hydroxide using a sodium acetate elution gradient. Sugar alcohols were analyzed using a CarboPac MA1 column which contains porous beads (8.5 µm diameter) of vinylbenzene chloride/divinylbenzene with alkyl quaternary ammonium functional groups. These columns were also operated under manufacturer-recommended conditions (2000 psi maximum) in sodium hydroxide using a sodium hydroxide elution gradient. The conditions used to separate most complex carbohydrates (polysaccharides and glycoconjugates) are given in Table 1. The conditions for separation of sugar alcohols and glycerol are given in Table 2. Conditions for most monosaccharide determinations are given in Table 3, while conditions for determination of mannose and xylose are given in Table 4.

TABLE 1

| Polysaccharide (Glycoconjugate) Determination | |
|---|---|
| Column: | CarboPac PA-1 |
| Gradient: | 150 mM NaOH |
|  | 0–500 mM NaOAc, 5–40 min. |
| Flow Rate: | 1.0 ml/min |
| Detector 1: | PED 1, Pulsed Amperometric Mode |

| Waveform | | Integration | |
|---|---|---|---|
| Time (sec) | Potential (V) | Begin (sec) | End (sec) |
| 0.00 | 0.10 | 0.30 | 0.50 |
| 0.50 | 0.10 | | |
| 0.51 | 0.60 | | |
| 0.59 | 0.60 | | |
| 0.60 | −0.60 | | |
| 0.65 | −0.60 | | |
| Detector 2: | VDM-II | | |
|  | Absorbance at 280 nm | | |

TABLE 2

| Sugar Alcohols (Alditols, Inositol) and Glycerol Determination | |
|---|---|
| Column: | CarboPac MA-1 |
| Gradient: | 150 mM NaOH, isocratic or |
|  | 300 mM NaOH, isocratic |
| Flow Rate: | 0.4 ml/min |
| Detector 1: | PED 1, Pulsed Amperometric Mode |

| Waveform | | Integration | |
|---|---|---|---|
| Time (sec) | Potential (V) | Begin (sec) | End (sec) |
| 0.00 | 0.05 | 0.20 | 0.40 |
| 0.40 | 0.05 | | |
| 0.41 | 0.70 | | |
| 0.60 | 0.70 | | |
| 0.61 | −0.15 | | |
| 1.00 | −0.15 | | |

TABLE 3

Monosaccharide Determination

| Column: | CarboPac PA-1 |
|---|---|
| Gradient: | 16 mM NaOH, isocratic |
| Flow Rate: | 1.0 ml/min |
| Detector 1: | PED 1, Pulsed Amperometric Mode |

| Waveform | | Integration | |
|---|---|---|---|
| Time (sec) | Potential (V) | Begin (sec) | End (sec) |
| 0.00 | 0.10 | 0.30 | 0.50 |
| 0.50 | 0.10 | | |
| 0.51 | 0.60 | | |
| 0.59 | 0.60 | | |
| 0.60 | −0.60 | | |
| 0.65 | −0.60 | | |

TABLE 4

Mannose and Xylose Determination

| Column: | CarboPac PA-1 |
|---|---|
| Gradient: | 75 mM NaOH, isocratic |
| Flow Rate: | 1.0 ml/min |
| Detector 1: | PED 1, Pulsed Amperometric Mode |

| Waveform | | Integration | |
|---|---|---|---|
| Time (sec) | Potential (V) | Begin (sec) | End (sec) |
| 0.00 | 0.10 | 0.30 | 0.50 |
| 0.50 | 0.10 | | |
| 0.51 | 0.60 | | |
| 0.59 | 0.60 | | |
| 0.60 | −0.60 | | |
| 0.65 | −0.60 | | |

The results presented below employed a pulsed amperometric detection (PAD) system. The current invention comprises the diagnostic usefulness of the presence and/or absence of certain glycoconjugates, as well as the timing of their appearance or disappearance. It must be appreciated that the exact method of detecting these carbohydrates is not central of the invention. Any other suitable detection system capable of resolving the eluted carbohydrates could be employed.

Nevertheless, a brief explanation of the PAD system is in order. PAD detects carbohydrates through the electrochemical oxidation of carbohydrate hydroxyl groups on a gold electrode surface. An effective oxidizing potential applied to a gold electrode, in contact with a carbohydrate solution at a high pH oxidizes hydroxyl groups, with the resulting current being a sensitive and accurate representation of the carbohydrate concentration down to about the 10 picomolar range. The PAD process is selective in that only certain compounds are capable of being oxidized at a particular electrode potential.

However, the carbohydrate oxidation products rapidly poison the electrode surface. This problem has been solved by briefly raising the electrode potential to a higher positive value to oxidize the gold surface and drive off the oxidized carbohydrates. Following this oxidation step, the electrode potential is lowered to regenerate the gold surface; finally, the electrode is returned to the measuring potential. This pulsed cycle is repeated over and over again.

HPAEC was used to analyze various extracted cell wall fractions of cotton in an attempt to correlate variations in the physical properties of cotton samples with possible variations in the chemical composition of extracted cell wall fractions. HPAEC provides the first available way to analyze monosaccharides and polysaccharides simultaneously. Initially, hot water extracts were made of cell wall material. An unexpectedly large amount of monosaccharides were revealed by HPAEC chromatography suggesting that the hot water was disrupting covalent bonds. Progressive studies were made of cooler and cooler water extractions. During this study it was discovered that cold water extracts of cotton fibers are unexpectedly rich in mono and polysaccharities. Traditionally it has been assumed that hot water extraction, at least, was required to release significant material from the cell wall.

The polysaccharides extracted by cold water appear to be of varying complexity. Generally smaller polysaccharides are referred to as "oligosaccharides" although no exact dividing line separates oligosaccharides from polysaccharides. Further, these analyses have shown that some of the extracted material have a protein component. Others may also have a lipid component. The common factor is the presence of oligo or polysaccharide which renders the compounds separable by HPAEC. In the following description "glycoconjugate" or "oligosaccharide" is used to describe these variable carbohydrates which may also contain protein and/or lipid.

Cotton fiber samples of known growth stages from plants grown under various conditions were analyzed. The general experimental protocol followed in these experiments is to tag each flower of a cotton plant as it opens (anthesis). In this way the cotton boils can later be harvested at a known time postanthesis. The harvesting times were generally 2, 3, 4, and 5+ weeks postanthesis in keeping with the cotton fiber development times as outlined above.

Once a boll has been harvested from the cotton plant, steps must be taken to prevent microbial deterioration or autolysis and to preserve the cotton fibers against any premature extraction of cell wall components. The preferred method is to freeze the cotton boll as quickly as possible after harvest. The boll may be rapidly taken to and placed within a freezer, preferably a low temperature unit that operates at or below −20° C. Alternatively, dry ice or liquid nitrogen can be taken into the field and the bolls frozen immediately upon harvesting. Currently, dry ice in a styrofoam or similarly insulated cold box represents the preferred method of postharvest freezing. The dry ice can be easily procured and transported into the cotton field. Large number of boils can be conveniently harvested and immediately frozen in this way.

Before analysis the bolls must be lyophilized to remove free water. The freeze-dried bolls can be easily opened and samples of fiber free of seeds, fruit wall (boll) and lint can be readily dissected out. Fibers may undergo further processing such as being pressed into sample pellets prior to extraction. The exact preprocessing does not appear critical as long as contamination of material from the boll or other sources is avoided.

Each fiber sample is then extracted with cold water. Typically 3–5 mg of fiber are extracted with 0.5 ml of water in a capped vial at 0° C. on an ice bath. To ensure complete extraction the vials are sonicated for 15 minutes with a Bransonic Ultrasonicator Bath set at 80 W.

FIG. 1 shows an idealized HPAEC profile of a sample of a cold water extract of cotton fibers taken from a 21-day postanthesis boll of cotton variety DPL54-15. This sample is from plants grown under optimal conditions in the southeastern United States and should be representative of normal plants in that area. This is a typical plot for this method showing response of the PAD system (y axis) versus retention time on the chromatographic column (x axis). The PAD method is quantitative so that area under a peak is directly proportional to the amount of carbohydrate comprising that peak.

The oligosaccharides (glycoconjugates) of interest in the cold water extracts are generally retained on the columns for less than 40 minutes under the typical analysis conditions. Monosaccharides generally emerge between 3–6 minutes. A sucrose peak 12 emerges from the column at about 10 minutes. Monosaccharides and disaccharides, like sucrose, tend to pass through the column more rapidly than the glycoconjugates that are the subject of the present invention.

Following the sucrose peak 12 is a first group of glycoconjugate peaks 14. These peaks 14 have been denoted as glycoconjugates 1 (GC1) and typically show a retention time of from about 14–17 minutes with a largest peak (GC1-2) 16 usually falling between 14–15 minutes. Analysis of a large number of cell wall extracts has shown that these major peaks are consistently present. It should be appreciated that variations in experimental conditions may cause the precise retention times to vary from run to run. However, the retention times can be normalized to known standards and to identified peaks such as the sucrose peak. Furthermore, the peaks can and are collected after they emerge from the column for further analysis which allows the unambiguous identification of each peak.

GC1 14 forms a "mountain range" of about 4–8 peaks on one side of a small "valley" 17, with a second group of peaks 18 known as glycoconjugates 2 (GC2) forming a range on the other side of the valley 17. GC2 18 generally ranges in retention time from about 18 to about 21 minutes with highest peaks (GC2—2, GC2-3) at about 19–20 minutes. The peaks have been named by their positions in each group with the highest peak 16 in GC1 being known as GC1-2 and the highest peak 20 in GC2 being known as GC2-3. As shown in the idealized plot of FIG. 1, the other peaks are named in a similar manner.

Although the exact origin of the carbohydrate peaks seen in the analyses of the cold water fractionations are not yet known, it is likely that they represent the cellular carbohydrate complexes used to synthesize the cell walls of the cotton fiber. Sucrose is a major transport carbohydrate of plants and is the primary photosynthate transported from a source (the leaves) to a sink (the growing cotton fiber). The glycoconjugate peaks that comprise the two groups of peaks could well represent carrier complexes of polysaccharides being assembled into substructures for transport to the growing cell wall of the fiber. Monosaccharide analyses of the various fractions indicate that the GC1 and GC2 fractions are rich in glycerol and inositol, suggesting carrier structures in which sugars (primarily glucose and mannose) are linked to these compounds, perhaps via the hydroxyl groups. The same chromatographic analysis used to detect glycoconjugates can and has been used to detect the presence of protein moieties by monitoring optical absorption at 280 nm. The present studies have shown that some of the suspected inositol/glycerol carriers also have a protein component as would be expected for biological carriers.

It is possible but not as likely that the oligosaccharides could represent pieces of cell wall detached by the extraction process. First, cold water extraction is not very likely to break covalent bonds or disrupt other interactions holding the cell wall together. Second, the appearance of each glycoconjugate peak is quite consistent and varies in amount at different growth stages. This would be more likely for a wall precursor, such as a prepolymerized sugar assembly, rather than a wall section torn from the already assembled wall.

Figure 2:
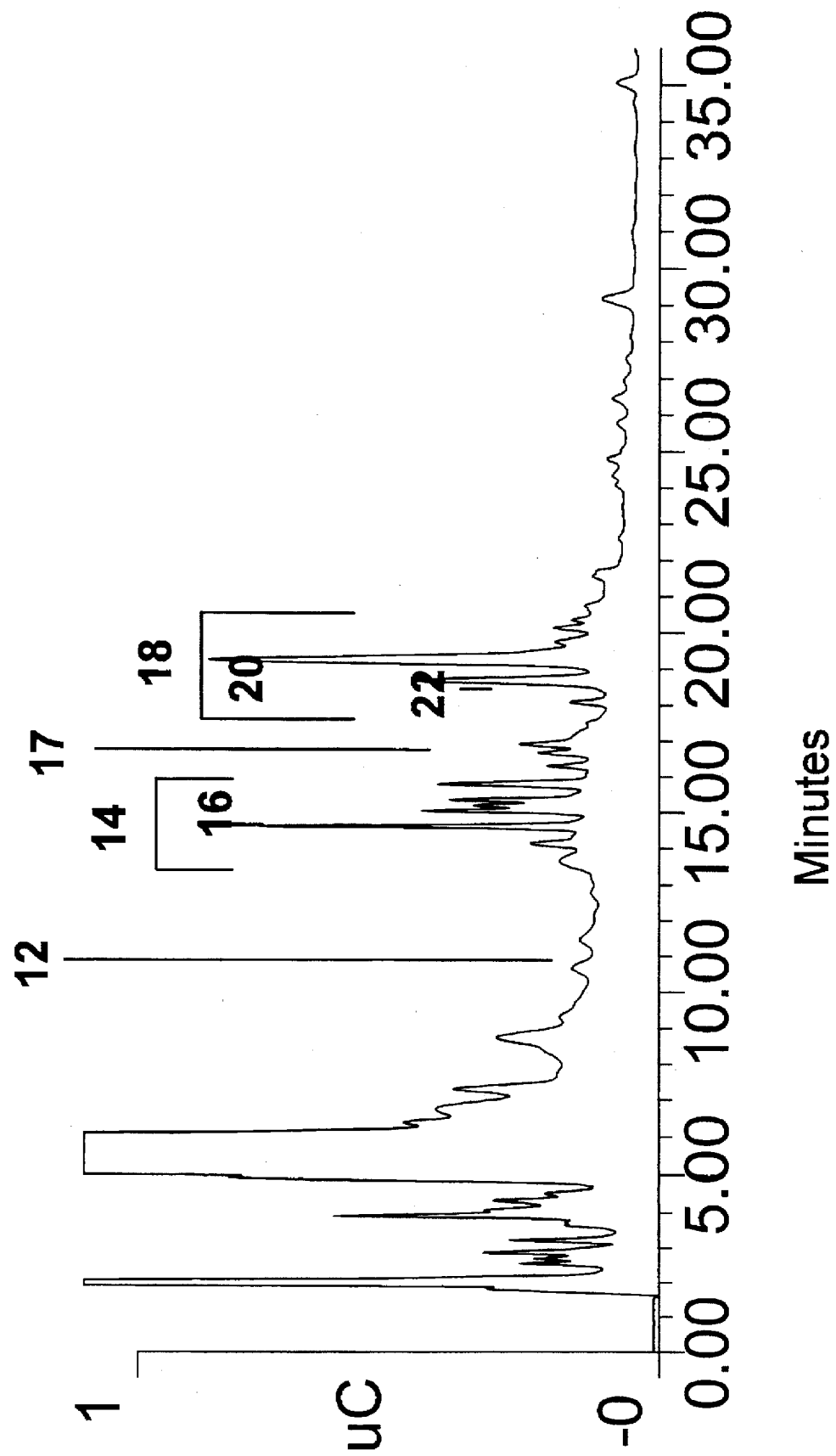
FIG. 2 shows an actual chromatogram of DPL5415 fibers 21 days postanthesis.
Figure 3:
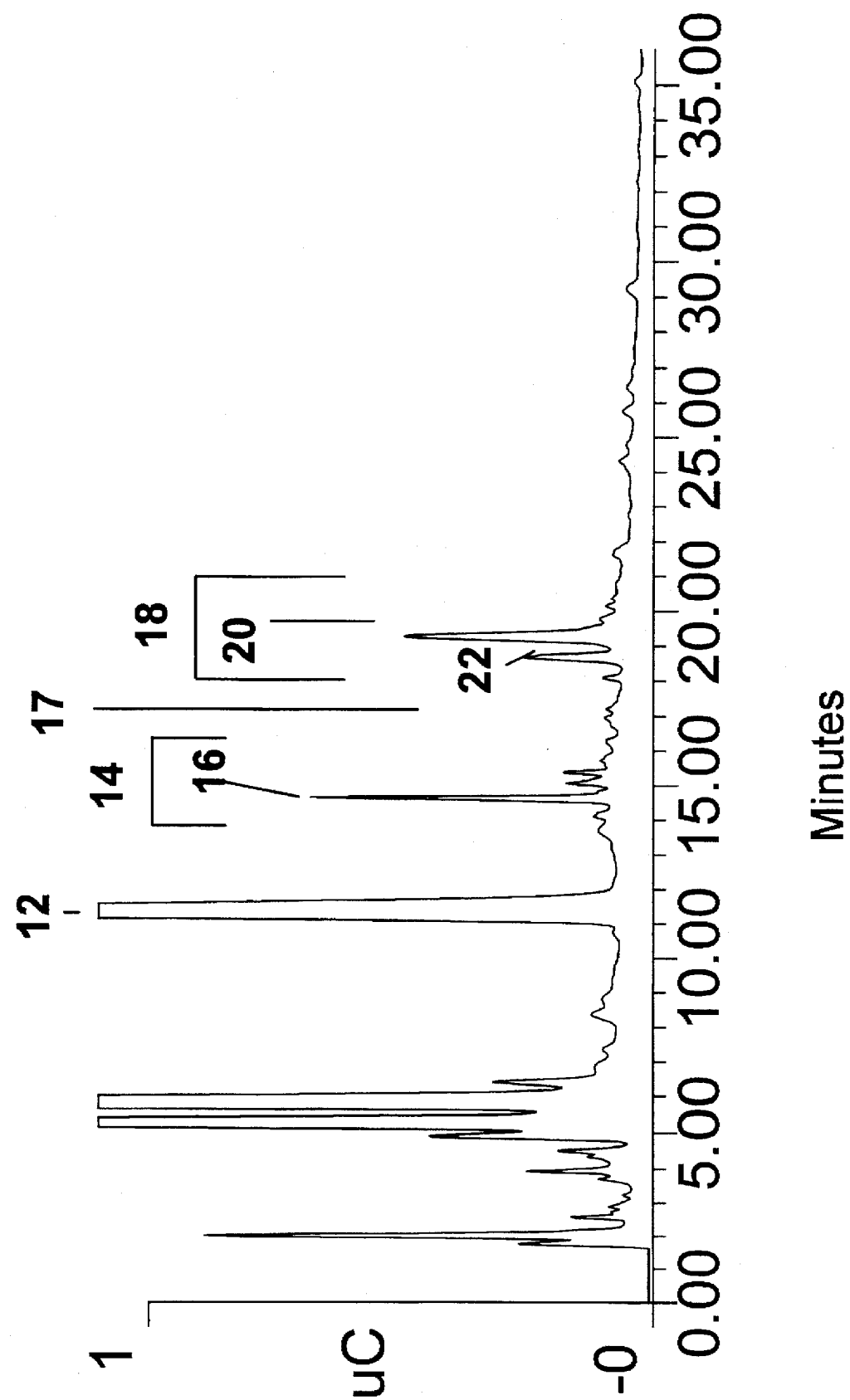
FIG. 3 shows an actual chromatogram of DPL5415 fibers 28 days postanthesis.

FIG. 2 shows an actual chromatogram of DPL5415 fibers 21 days postanthesis (DPA). This is typical of the "raw" chromatogram from which FIG. 1 was developed. FIG. 3 shows an analysis of normally grown DPL5415 fibers 28 days postanthesis. Compared to FIG. 2, there is less overall polysaccharide extracted. Most probably this is at least partially an artifact of the standardization of the samples by weight of the fibers extracted. Between day 21 and day 28 the total mass of the cell wall increases substantially, but if the actual wall synthesizing complexes remain approximately stable in amount, they will appear to diminish when expressed on a total mass of cell wall basis.

Figure 4:
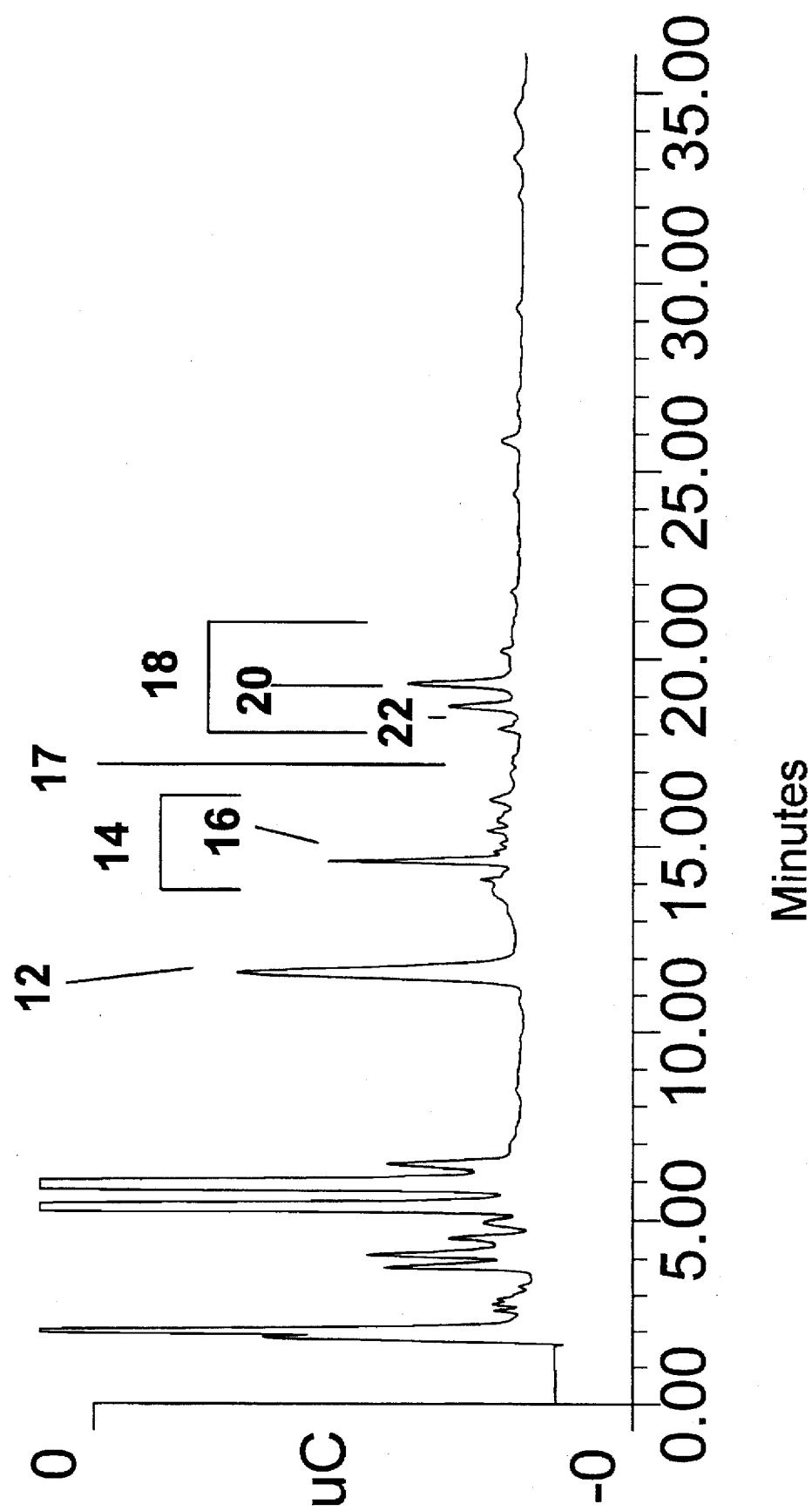
FIG. 4 shows an actual chromatogram of DPL5415 fibers 42 days postanthesis.

In FIG. 3 the GC1-2 peak 16 is now an even more dominant part of GC1. That is, the other peaks of GC1 are decreased in abundance relative to the GC1-2 peak 16. The GC2-3 peak 20 appears increased relative to the GC2—2 peak 22. These changes continue in FIG. 4 which represents fibers from normally grown DPL5415 42 DPA. By this time the cotton fibers are approaching maturity with only secondary cell wall synthesis occurring. While the total amount of polysaccharide extracted is reduced compared to FIG. 3 (consistent with the increase in wall mass), a sucrose peak 12 is still considerable, indicating that the plant is still delivering a considerable amount of photosynthate to the maturing boll. The GC2-3 peak 20 appears reduced relative to the GC2—2 peak 22.

Figure 5:
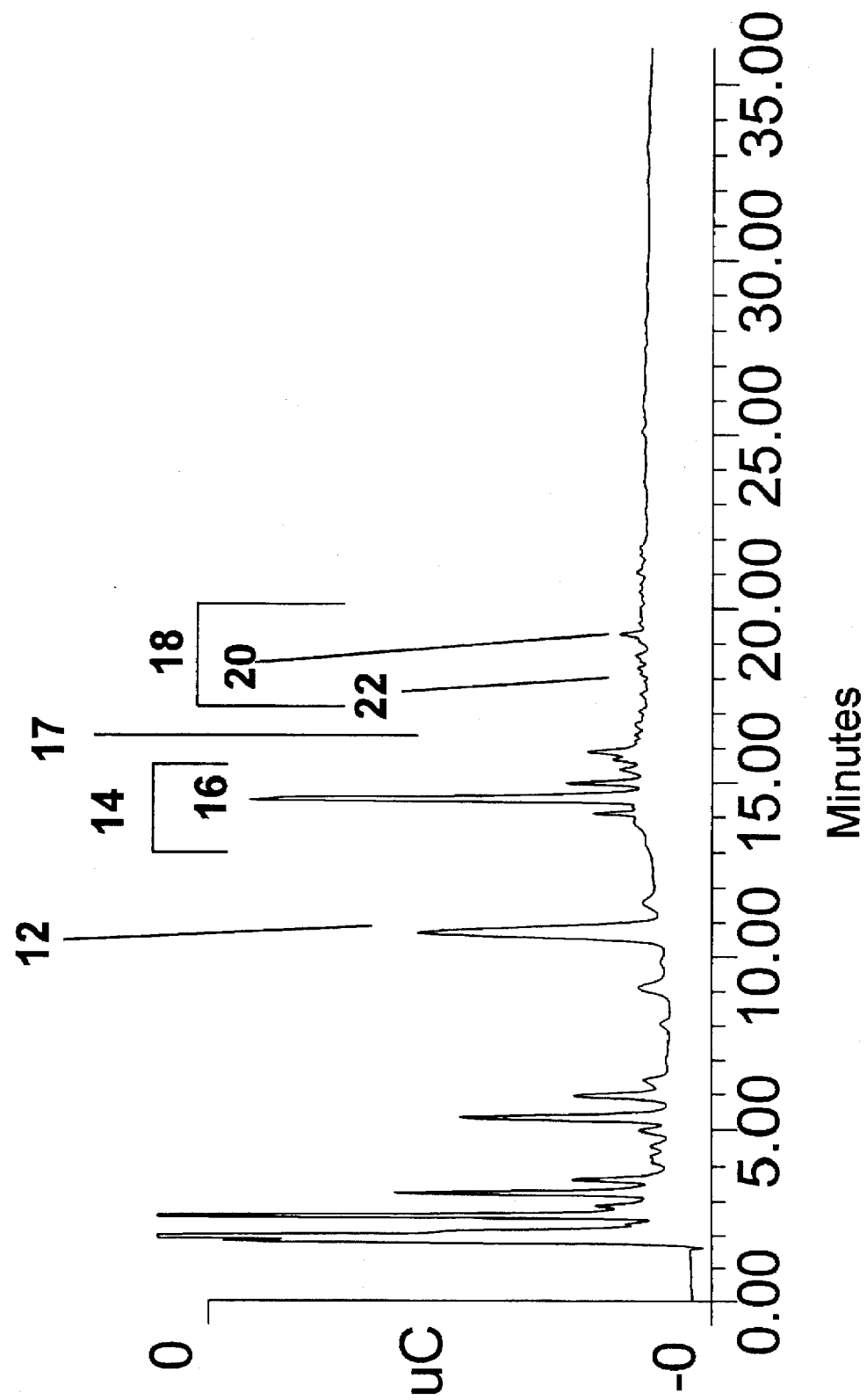
FIG. 5 shows an actual chromatogram of DPL5415 fibers 56 days postanthesis.

Finally, FIG. 5 shows polysaccharides extracted from fibers of a fully mature DPL5415 boll at 56 DPA. At this point the boll is essentially dead and photosynthate is no longer being transported into it. All cellular activity should have ceased so that any carbohydrates extracted by cold water probably represent either residual synthetic complexes that were not incorporated into the wall before cell death or a background level of covalently linked carbohydrates that are detached by the extraction process. Consistent with this picture is the very low level of the sucrose peak 12. GC1 14 is reduced relative to FIG. 4, while GC2 18 remains low.

One factor that should be kept in mind in interpreting the foregoing results is the cell wall mass problem mentioned above. Both glycoconjugate peak groups seem to be associated with synthesis of the primary cell wall. As the fiber nears maturity the vast majority of the wall material present represents secondary wall. If either or both of the peak groups are being extracted solely from primary wall or is a precursor of primary wall, their apparent abundance will be greatly reduced since only a tiny proportion of the 3–5 mg of wall extracted is primary cell wall.

This pattern is consistent with the polysaccharides of GC1 14 representing precursors of both primary and secondary cell wall synthesis and with the polysaccharides of GC2 18 representing constituents (possibly derived from GC1 14) that are used mostly in primary cell synthesis. Primary cell wall synthesis peaks between two and three weeks, and after four weeks or so secondary cell wall synthesis largely predominates. Therefore, under normal growth conditions the GC2-3 peak 20 reaches its maximum around the time that secondary wall deposition begins to predominate. Since the GC1-2 peak 16 probably represents material used in both primary and secondary wall synthesis, that peak remains prevalent even after most primary wall synthesis ceases.

Figure 6:
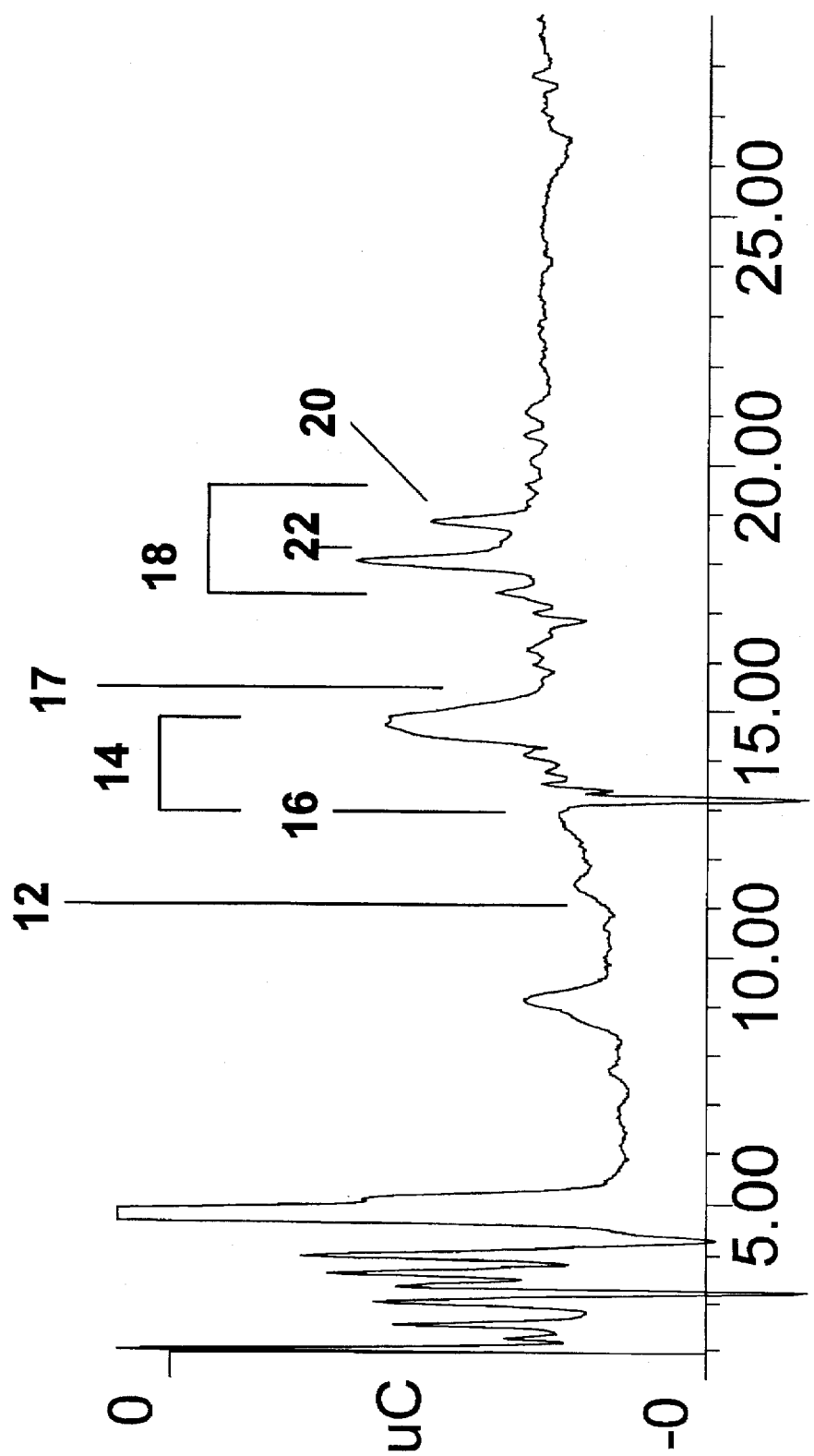
FIG. 6 shows a difference plot of the carbohydrates extracted from mature bolls of the cotton variety Maxxa grown under optimal conditions versus under drought conditions.

Various plots of cotton grown under normal and under extreme water stress were compared to identify which glycoconjugates were altered under these conditions. When mature cotton bolls from normally irrigated plants of cotton variety Maxxa were compared with those grown under drought stress conditions, the following peaks were most strongly affected by stress: GC1-2, GC1-3 to GC1-5 (poorly resolved), GC1-6, GC2—2, GC2-3, and GC2-5. FIG. 6 shows a difference plot (drought stressed results subtracted from normal irrigation results) in which the differences in the above mentioned peaks is apparent. A negative peak indicates that there was more of that peak in the drought stressed cotton than in the normal cotton.

As mentioned earlier, one of the advantages of the PAD detection system is that for any particular polysaccharide the area under a peak is directly proportional to the amount of that polysaccharide present. Since different sugars may produce different PAD detector responses, it is not possible to make quantitative comparisons between two different polysaccharides. Furthermore, the large changes in amounts of polysaccharide extracted at different growth stages is difficult to represent on a single plot. This problem can be partially avoided by plotting the overall results on a log scale. In this way all the results can be readily placed on one plot. However, one must remember that large changes are minimized at higher log cycles.

Figure 7:
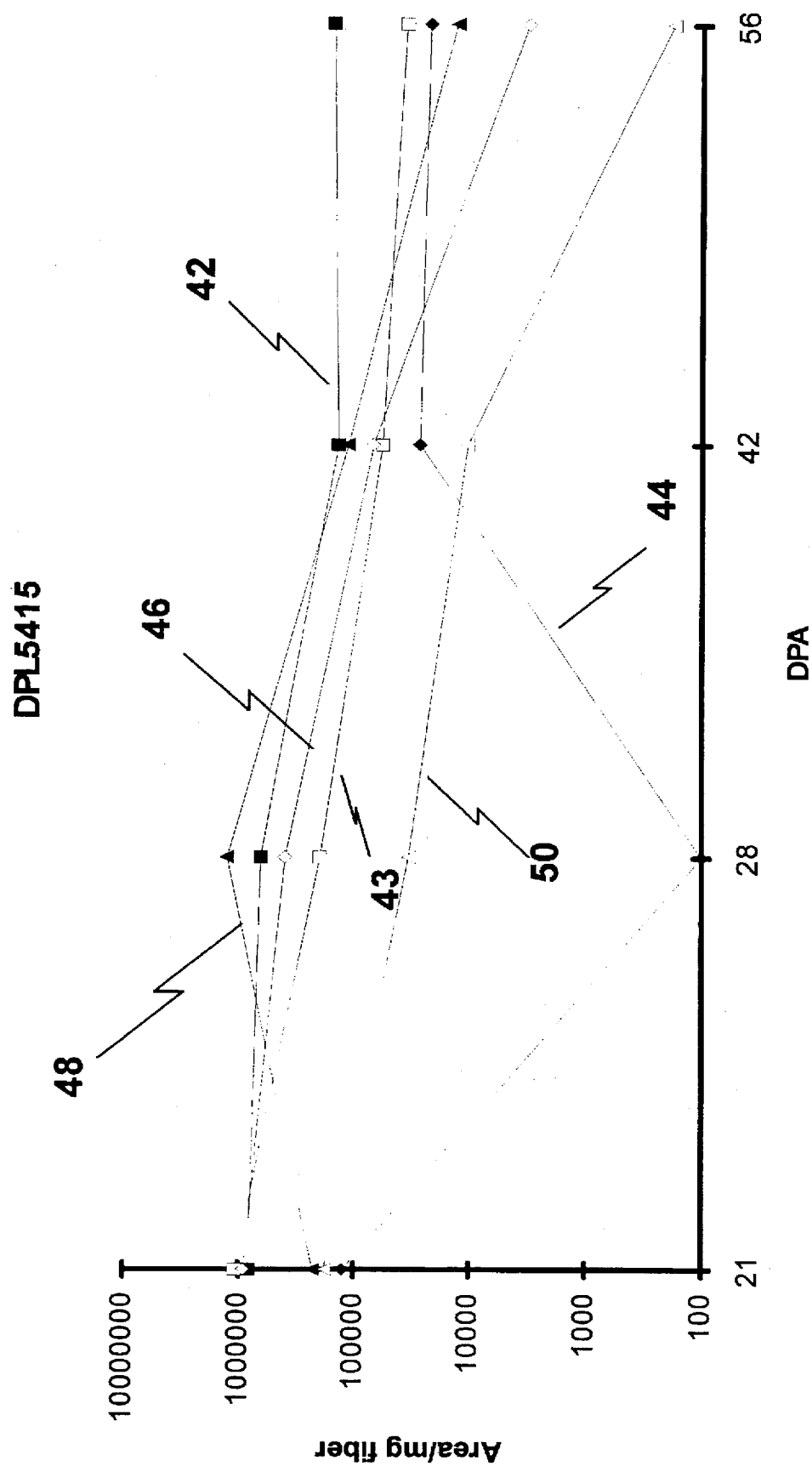
FIG. 7 shows the DPL5415 samples of FIGS. 2–5 showing stress responsive peaks identified in FIG. 6 plotted on a log scale.

In FIG. 7 the DPL5415 samples shown in FIGS. 2-5 are plotted on a log scale. Only the peaks which were found to respond most strongly to growth conditions are shown. A trace 42 for GC1-2 shows a fairly consistent level with some increase for the 56 DPA point. A trace 43 for GC1-3 to 1-5 closely tracks GC1-2. A trace 44 for GC1-6 also shows a marked drop at 28 days followed by a later recovery. On the other hand, a trace 46 for peak GC2—2 shows a fairly constant rate of decrease days 21 and 56. This plot also shows that a trace 48 for GC2-3 peaks at 28 DPA, a behavior reciprocal to GC114 6, while a trace 50 for GC2-5 falls off somewhat more sharply.

Figure 8:
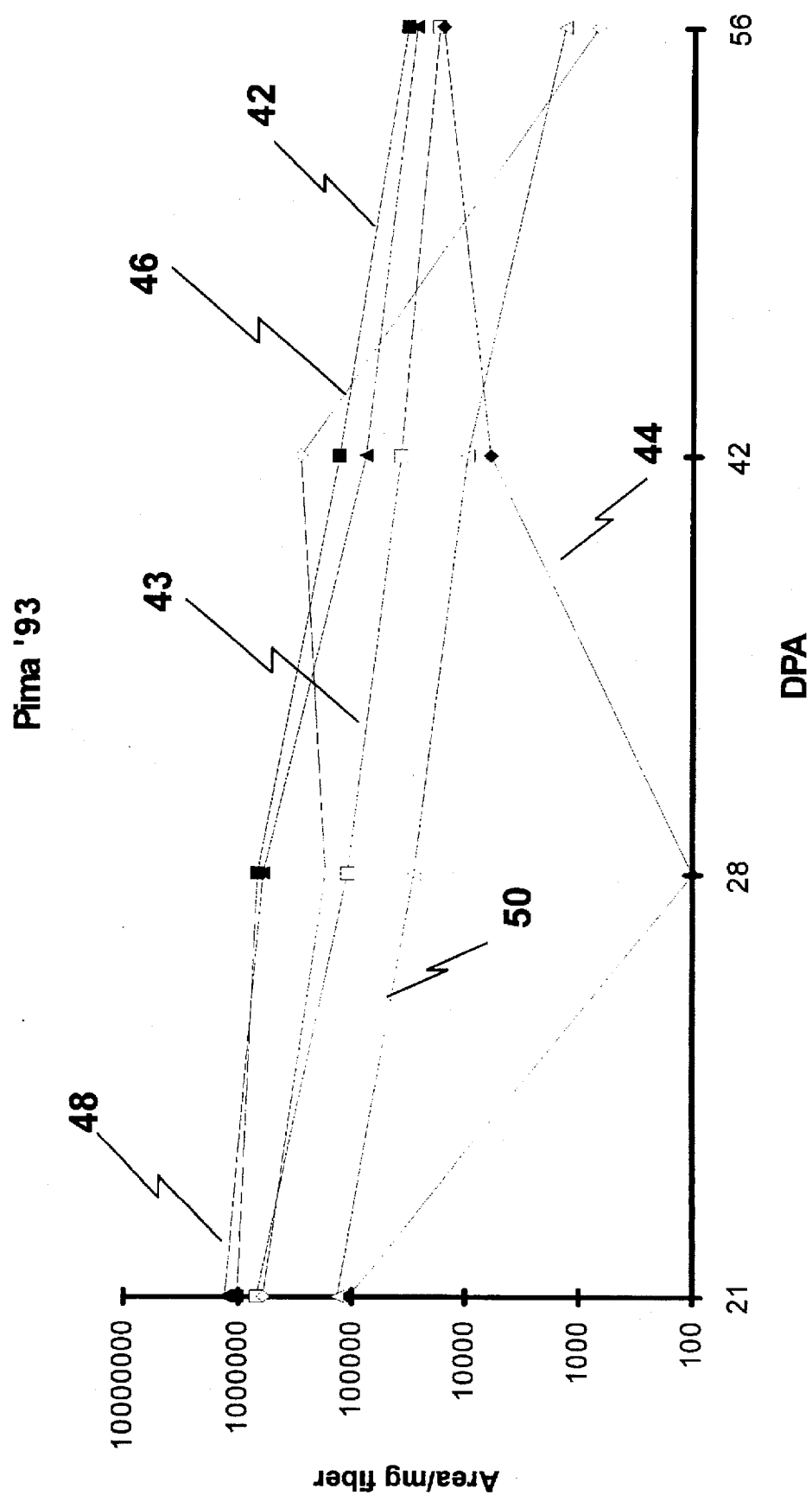
FIG. 8 shows samples of cotton variety Pima S-6 grown under suboptimal temperature conditions showing stress responsive peaks plotted on a log scale.

The results of FIG. 7 should be compared to FIG. 8, which represents a similar plot of a second cotton variety, Pima S-6. This variety was grown under somewhat suboptimal temperature conditions. Here the trace 42 for GC1-2 shows slightly more of an overall drop. The trace 43 for GC1-3 to 1-5 tracks trace 42 (GC1-2) very closely as it does in FIG. 6. The trace 44 for GC1-6 is similar to that of FIG. 7 but appear slightly reduced around day 42. The trace 46 for GC2—2 shows an increase around day 42, while the trace 48 for GC2-3 is relatively similar to that of FIG. 7. Finally the trace 50 for GC2-5 is somewhat elevated at day 56 as compared to FIG. 7. These data indicate that the profiles of these glycoconjugate peaks are sensitive indicators of growth conditions.

Figure 9:
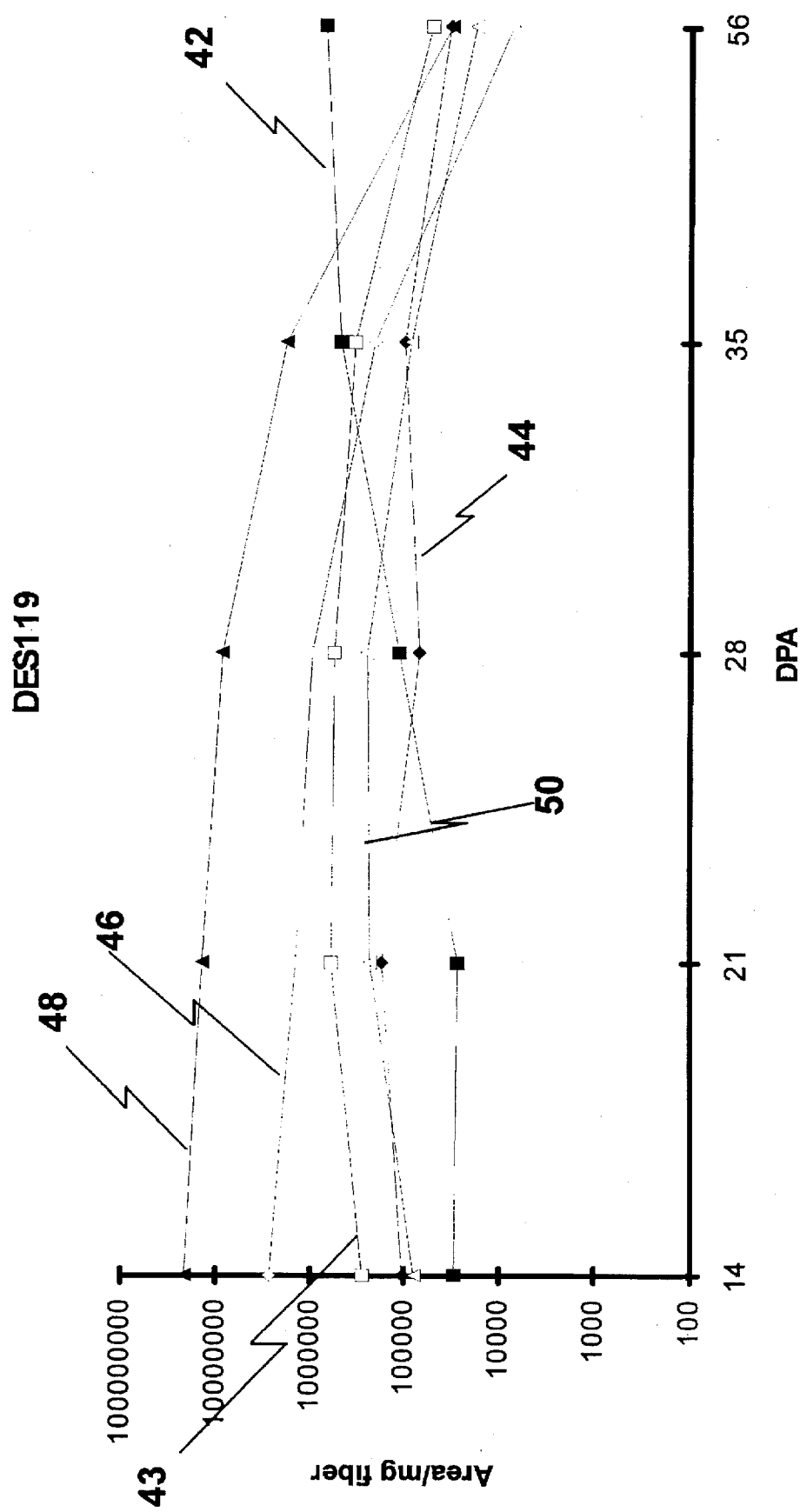
FIG. 9 shows samples of cotton variety DES119 grown under suboptimal temperature conditions showing stress responsive peaks plotted on a log scale.

The alteration of the oligosaccharicle/glycoconjugate peaks are even more pronounced in FIG. 9, which shows cotton variety DES119 grown under suboptimal cool morning temperatures early in the growth season. Generally, cotton requires high growth temperatures, especially warm night temperatures. In the figure, the trace 42 for GC1-2 is markedly decreased at early time points and increased at late time points. The trace 44 for GC1-6 does not have the normal dip at 28 days. The trace 43 for GC1-3 to 1-5 does not track GC1-2 as in FIG. 7. The trace 46 for GC2—2 is slightly depressed as compared to FIG. 7. The trace 48 for GC2-3 is somewhat elevated, while the trace 50 for GC2-5 shows an elevation, particularly between days 21 and 35.

While the exact behavior of the various fractions may vary slightly from cotton variety to cotton variety, it is clear that changes in growth conditions result in reproducible alterations. Under optimal growth conditions GC1 peaks tend to be relatively high at early time points and, except for a sharp clip of GC1-6 at 28 days, remain fairly constant for the remainder of the growth cycle. This is consistent with the theory that the GC1 material is a normal precursor to both primary and secondary cell wall synthesis and, hence, remains constant under normal conditions. However, when conditions are somewhat disturbed, some parts of GC1 may actually begin at a lower level and increase through the growth cycle. The usual dip at day 28 for GC1-6 could represent the initiation of some additional process such as secondary wall growth that temporarily depletes this precursor.

On the other hand, the GC2 material seems to be more tightly linked to primary cell growth and decreases as the cotton approaches maturity. Under disturbed growth conditions the GC2 material may actually peak at some time later than 28 DPA and then decrease. In summary, the important factors appear to be the relative abundance of GC1 versus GC2 overall and whether GC1 components are relatively constant (normal) with GC2 components slowly decreasing over time (normal), or whether either or both GC1 and GC2 show an increase over time (abnormal).

Figure 10:
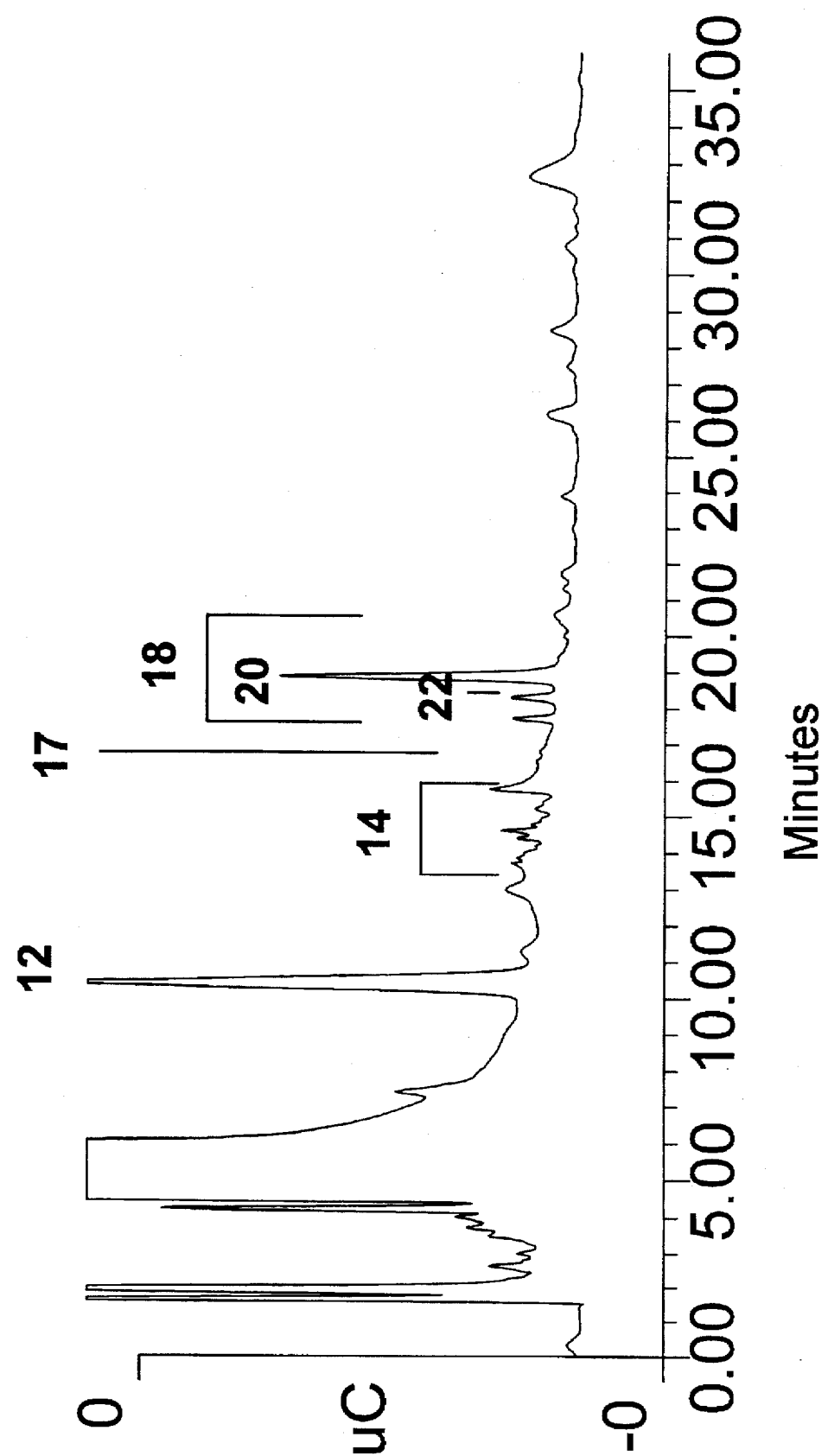
FIG. 10 shows a chromatogram of carbohydrates extracted from eight day postanthesis fibers of cotton variety Maxxa grown with normal irrigation.
Figure 11:
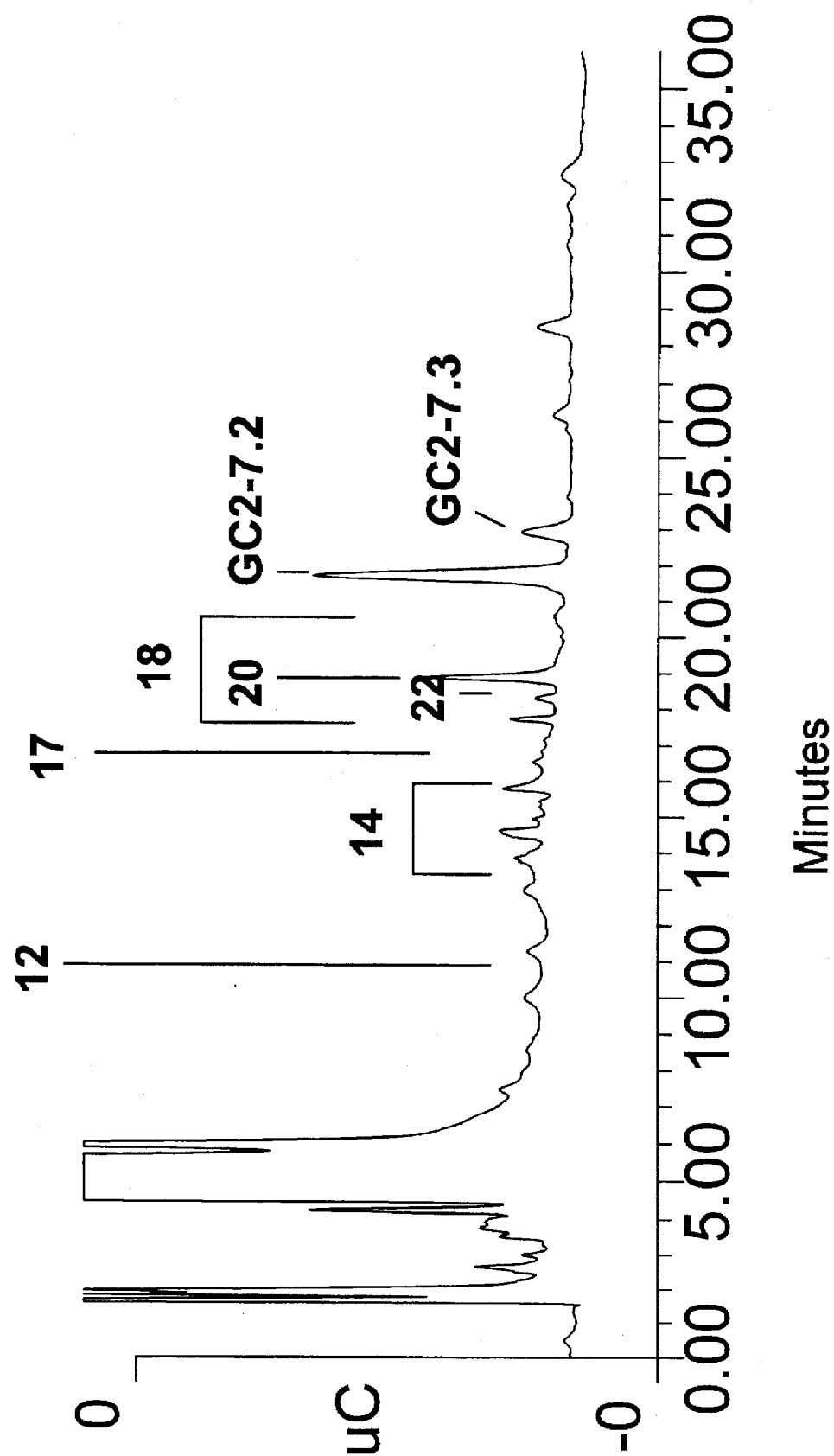
FIG. 11 shows a chromatogram of carbohydrates extracted from eight day postanthesis fibers of cotton variety Maxxa grown under water stress conditions.

The proper development of cotton fibers appears to be extremely sensitive to any water shortage. FIGS. 10 and 11 show the carbohydrates from very young cotton bolls of cotton variety Maxxa at 8-10 DPA. The cotton in both figures received a normal irrigation in mid-June. The next scheduled irrigation was on July 21, and the samples were collected on July 25—only four days after the irrigation.

The cotton in FIG. 10 received the July 21 irrigation, while that in FIG. 11 did not. As might be expected in a very early sample (maximal primary cell wall synthesis), GC2—2 and GC2-3 appear very prominently in FIG. 10. But a four-day difference in irrigation causes the cotton in FIG. 11 to show a dramatic increase in two peaks that are normally insignificant, GC2-7.2 and GC2-7.3. It would appear that metabolic disturbance of the plant caused by drought has caused normally insignificant glycoconjugates to accumulate. Presumably these compounds exist in a very dynamic pool that is turning over rapidly, possibly by becoming permanently inserted into the wall. The water stress disturbs this process. This could be due to an effect on photosynthesis (i.e., alteration of the source of the carbohydrates) or on cell elongation due to lack of turgor pressure (i.e., alteration of the ultimate sink for the GC2 oligosaccharides).

It is not yet known whether the cotton in FIG. 10 also showed oligosaccharides characteristic of drought stress prior to the irrigation and then recovered within the four subsequent days after the irrigation, or whether the abnormality seen in FIG. 11 did not develop until after July 21, the irrigation date. In either case, it is clear that measurement of GC2-7.2 and GC2-7.3 in very young cotton bolls is a sensitive indicator of water stress. Using the present invention it will be possible to measure the response of cotton plants so that irrigations can be fine-tuned to produce optimum cotton growth, rather than merely irrigating according to the calendar.

Another way of looking at the overall results is to consider that if secondary cell wall deposition is disturbed, say through unfavorable growth condition, the proportion of primary cell wall in the mature fiber may actually be increased resulting in a prevalence of GC2 peaks 18. In any case, the present invention provides a sensitive method of detecting environmental stress such as water stress. Other types of stress such as lack or over abundance of light, lack of mineral nutrients or improper growth temperature would be expected to produce similar or related results.

The experiments leading to the present invention employ analysis of cotton fibers of known ages. In actual field practice of the invention it is relatively simple to tag a flower on the day of opening so that bolls of known ages can be later collected. Alternatively, comparable knowledge of boll age can be collected by simultaneously harvesting a series of bolls from one plant. A cotton plant is indeterminate, producing a series of flowers on higher and higher branches as the plant grows. Thus, at any time the position of a boll on a plant is an indicator of the boll's age. Furthermore, collection of such a series produces, to some extent, a historical record or the stress conditions in the immediate past. That is, some bolls may have grown primarily when the plant was experiencing drought, and this fact will be reflected in the glycoconjugates/oligosaccharides extracted from those bolls. Other boils may have grown primarily before or after a drought period and, hence, will give different glycoconjugate results.

Although chromatography is presently the preferred way of detecting alterations in glycoconjugate/oligosaccharides, other simpler systems are being developed. For example, monoclonal antibodies can be produced to identify unique oligosaccharides. Therefore, simple colorimetric antibody-based tests could be developed to identify increases in GC2–7.3 or some similar stress responsive oligosaccharide. This would allow field testing by farmers.

Figure 12:
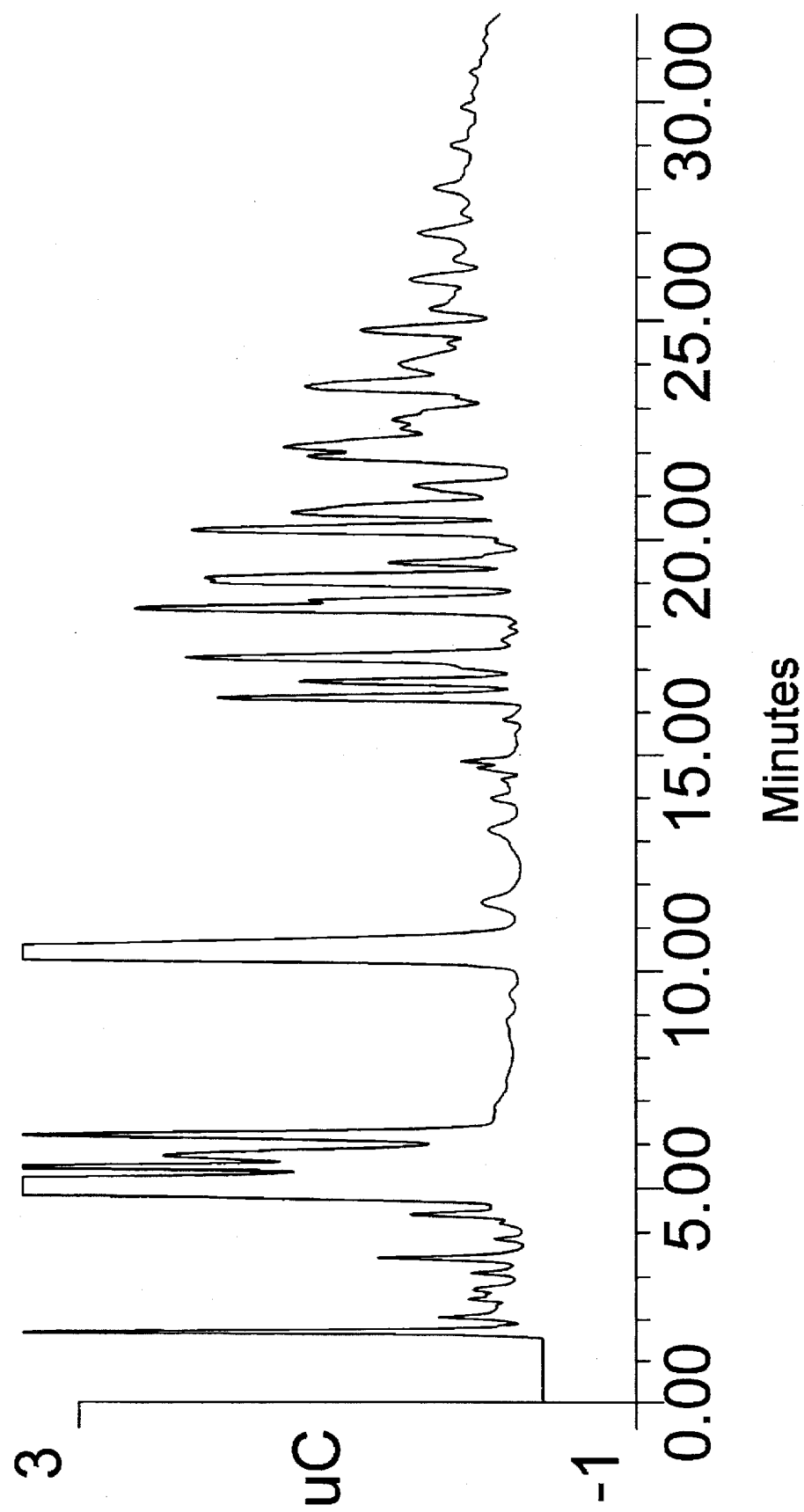
FIG. 12 shows a chromatogram of carbohydrates from tissue of Yucca, extracted and analyzed according to the present invention illustrating that the carbohydrates identified as part of the present invention are present in a variety of plants.

Since virtually all flowering plants have similar cell wall constituents, it is expected that the present invention can be directly applied to virtually any plant to detect the presence of environmental stress. Of course, it will be necessary to run a variety of samples of plants grown under different growing conditions to establish a standard profile for each plant type to be monitored. However, it is likely that closely related species of plant will be very similar. Also, it is likely that at least some of the overall patterns established in cotton will be directly applicable to other plants. FIG. 12 show a chromatogram of the glycoconjugates/oligosaccharides extracted from the cell walls of Yucca. A considerable number of the peaks appear to be similar to those of cotton.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method for determining a presence of environmental stress in cotton plants so that the stress can be alleviated before cotton fiber yield and quality is impacted, the method comprising the steps of:

providing a first population of cotton plants grown under optimum conditions and a second population of cotton plants grown under stress conditions;

harvesting, from both the first population and the second population, a series of cotton bolls at predetermined intervals, the intervals measured from a day of flowering of each boll;

preserving the harvested cotton bolls for analysis;

removing cotton fibers from the preserved cotton bolls;

extracting a predetermined weight of removed fibers in a predetermined volume of water;

conducting an analysis of material extracted from the removed fibers to detect characteristics and quantities of glycoconjugate polysaccharides present, said polysaccharides being distinguishable from monosaccharides and disaccharides;

making a determination of a glycoconjugate profile for normally grown plants and a stress glycoconjugate profile for plants grown under stress by plotting by time the analyses of the material extracted from fibers of the first population and the analyses of the material extracted from fibers of the second population;

harvesting, preserving, extracting, conducting an analysis and making a glycoconjugate profile of a third population from unknown growth conditions; and deciding whether the third profile more closely resembles the profile from the first or the second population, thereby determining whether the third population is experiencing stress.

2. The method of claim 1, wherein determination of stress includes comparing a first group of glycoconjugate peaks which elutes first from a column with a second group of glycoconjugate peaks which elutes later than the first group.

3. The method of claim 1, wherein the extracted material is analyzed using a column of polystyrene/divinylbenzene cross-linked latex microbeads having quaternary amine functional groups.

4. The method of claim 3, wherein the column is eluted with a sodium acetate gradient in sodium hydroxide.

5. The method of claim 3, wherein determination of stress includes comparing a first group of glycoconjugate peaks which elutes first from the column with a second group of glycoconjugate peaks which elutes later than the first group.

6. The method of claim 5, wherein the first group elutes between about 14 and about 17 minutes and the second group elutes between about 18 and about 35 minutes.

7. A method for determining a presence of water stress in cotton plants so that the water stress can be alleviated before cotton fiber yield and quality is impacted, the method comprising the steps of:

providing a first population of cotton plants grown under optimum conditions and a second population of cotton plants grown under water stress conditions;

harvesting, from both the first and the second populations, a series of cotton bolls at predetermined intervals from a day of flowering;

preserving the harvested cotton bolls for analysis by freezing and lyophilizing;

removing cotton fibers from the lyophilized cotton bolls;

extracting a predetermined weight of removed fibers in a predetermined volume of water at ice temperature;

analyzing the material extracted from the removed fibers using high pH anion exchange chromatography to detect characteristics and quantities of glycoconjugate polysaccharides present, said polysaccharides being distinguishable from monosaccharides and disaccharides;

making a determination of a normal glycoconjugate profile and a water stress glycoconjugate profile by plotting by time the analyses of the material extracted from fibers from the first population with the analysis of the material extracted from fibers from the second population;

harvesting, preserving, extracting, conducting an analysis and making a glycoconjugate profile of a third population from unknown growth conditions; and deciding whether the third profile more closely resembles the profile from the first population or from the second population, thereby determining whether the third population is experiencing water stress.

8. The method of claim 7, wherein determination of stress includes comparing a first group of glycoconjugate peaks which elutes first from a column with a second group of glycoconjugate peaks which elutes later than the first group.

9. The method of claim 7, wherein the column is eluted with a sodium acetate gradient in sodium hydroxide.

10. The method of claim 7, wherein the extracted material is analyzed using a column of polystyrene/divinylbenzene cross-linked latex microbeads having quaternary amine functional groups.

11. The method of claim 10, wherein determination of stress includes comparing a first group of glycoconjugate peaks which elutes first from the column with a second group of glycoconjugate peaks which elutes later than the first group.

12. The method of claim 11, wherein the first group elutes between about 14 and about 17 minutes and the second group elutes between about 18 and about 35 minutes.

13. A method for determining a presence of water stress in cotton plants so that the water stress can be alleviated before cotton fiber yield and quality is impacted, the method comprising the steps of:

extracting a predetermined weight of cotton fibers from bolls of a known age in a predetermined volume of water at ice temperature;

analyzing material extracted from the cotton fibers using high pH artion exchange chromatography to detect characteristics and quantities of glycoconjugate polysaccharides present, said polysaccharides being distinguishable from monosaccharides and disaccharides;

identifying a first group of glycoconjugate peaks that elutes first and a second group of glycoconjugate peaks that elutes later;

comparing the relative abundance of the first group and the second group to levels expected in fibers from control bolls of the known age, thereby determining whether the cotton plant is experiencing water stress.

* * * * *